United States Patent [19]

Cerra

[11] Patent Number: 5,353,803
[45] Date of Patent: Oct. 11, 1994

[54] APPARATUS AND METHOD FOR IMMEDIATE DIAGNOSIS OF VAGINAL YEAST INFECTIONS

[76] Inventor: Michael C. Cerra, 3052 Marston Way, San Jose, Calif. 95148

[21] Appl. No.: 79,329

[22] Filed: Jun. 18, 1993

[51] Int. Cl.$^5$ .............................. A61B 10/00
[52] U.S. Cl. ............................ 128/749; 128/636; 206/569
[58] Field of Search ............... 128/749, 759, 632, 633, 128/636, 665; 206/569

[56] References Cited

U.S. PATENT DOCUMENTS

| | | | |
|---|---|---|---|
| 3,999,948 | 12/1976 | Deindoerfer et al. | 128/636 |
| 4,195,059 | 3/1980 | Whitcher et al. | 206/569 |
| 4,803,048 | 2/1989 | Nason | 206/569 |
| 4,862,899 | 9/1989 | Bucaro | 128/759 |
| 4,953,560 | 9/1990 | Samuels | 124/759 |
| 5,143,210 | 9/1992 | Warwick et al. | 206/569 |

OTHER PUBLICATIONS

Bodey; Candidiasis—Pathogensis, Diagnosis, and Treatment; 2d ed. 1983; pp. 225, 230, 237–38.
F. C. Odds; "Genital candidosis"; 7 Clinical and Experimental Dermatology (1982); pp. 345–354 1982.
E. Houang; "Fluconazole in recurrent vaginal candidias: preliminary results of a double-blind, randomized clinic trial"; 1989 Royal Soc. Medicine Services Int'l Cong. and Symp. Series No. 160; pp. 33–34.
Baron and Finegold; Diagnostic Mcirobiology (1990), Procedure 7.5.
Hageage and Harrington, "Use of Calcofluor White in Clinical Mycology", 15 Laboratory Medicine (1984), pp. 109, 110, 112.
Hector and Braun, "A 96-Well Epifluorescence Assay for Rapid Assessment of Compounds Inhibitory to Candida spp.", 24 J. Clinical Microbiology (1986), pp. 620–624.

*Primary Examiner*—Max Hindenburg
*Attorney, Agent, or Firm*—David H. Jaffer

[57] ABSTRACT

Apparatus and method for immediate diagnosis of exudative vaginal yeast infections, using a sample of vaginal discharge, dying the yeast present in the discharge with a fluorescent dye specifically sensitive to yeast, and subjecting the dye to ultraviolet radiation to determine the level of visible fluorescence, with the level of fluorescence indicating the presence or absence of the high number of yeast associated with a vaginal infection.

20 Claims, 1 Drawing Sheet

U.S. Patent  Oct. 11, 1994  5,353,803
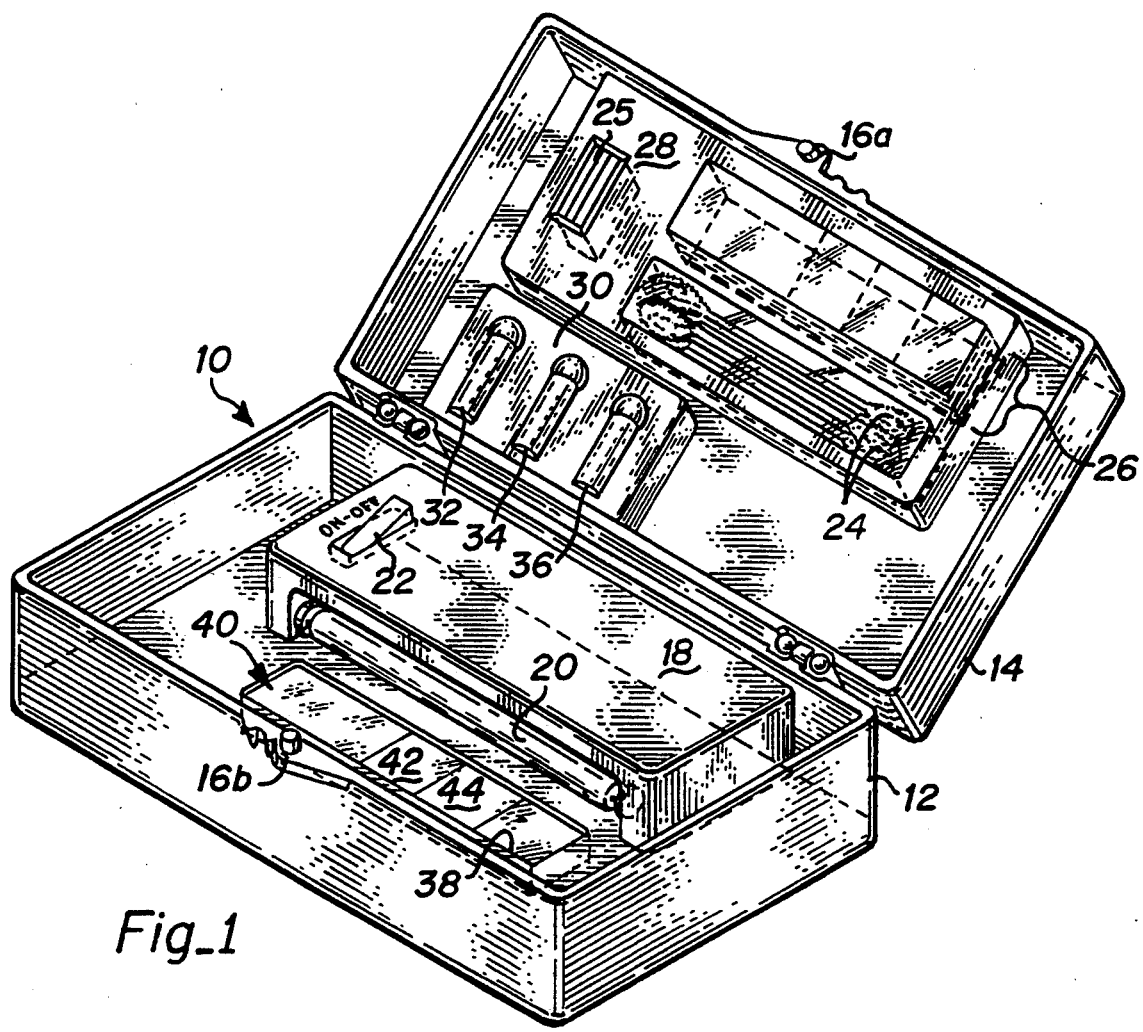
Fig_1
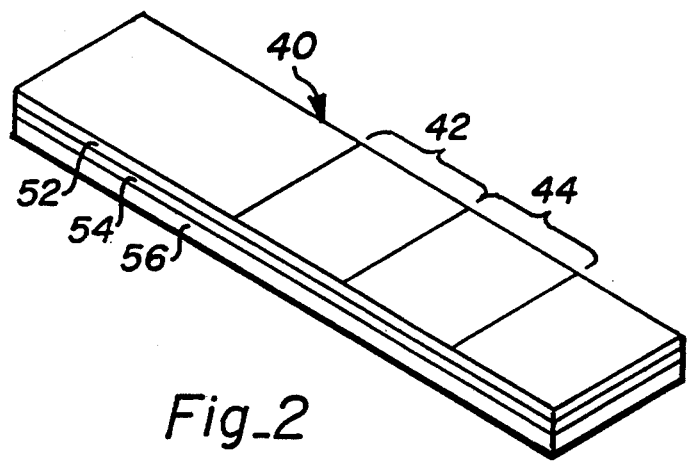
Fig_2

APPARATUS AND METHOD FOR IMMEDIATE DIAGNOSIS OF VAGINAL YEAST INFECTIONS

BACKGROUND OF THE INVENTION

1. Field of the Invention

The present invention relates generally to a method and apparatus for immediate diagnosis of exudative vaginal yeast infections. In particular, this invention relates to a method and apparatus which permit diagnosis or ruling-out of vaginal yeast infections without culturing yeast, thereby permitting immediate diagnosis through fluorescence of a dyed sample of the vaginal exudate.

2. Brief Description of the Prior Art

Vaginal yeast infections are a common problem affecting women of all ages. Vaginal anti-yeast prescriptions numbered 13 million in 1990 in the U.S. The infection results from the overgrowth of yeast which are often normally present but in much smaller numbers. The symptoms of a yeast infection include vaginal itching, discharge, soreness, irritation or burning. Since a vaginal yeast infection is strictly due to the presence of large numbers of the responsible organism, diagnosis and treatment would seem to be simple. However, other more serious vaginal infections can present a similar clinical picture which usually includes local itching, a vaginal discharge, and possibly abdominal pain and fever. For example, bacterial vaginosis, bacterial trichomoniasis, chlamydial infections, and gonorrhea can resemble yeast infections, especially to women without medical training.

Presently, over-the-counter anti-yeast medications have been approved for treating vaginal yeast infections. The availability of these medications encourages women to self-diagnose and self-treat a potentially serious medical problem, without a medical examination, based upon a hope that the problem may simply be due to yeast. Self-diagnosis without diagnostic data is dangerous, since proper treatment may be delayed or the wrong treatment may be undertaken, possibly leading to invasive infections or sterility due to pelvic inflammatory disease.

The prior art teaches confirmation of the presence of an infectious organism through the use of a variety of culture techniques. U.S. Pat. Nos. 3,368,569 and 4,953,560 teach use of a swab including a culture medium. U.S. Pat. Nos. 3,616,265, 4,653,510, and 4,485,824 teach a variety of swabs and culture mediums for simplification of transferring a vaginal secretion to a culture medium. All of these techniques require that the yeast be cultured, a technique that requires incubation of the yeast for 12 to 24 hours under aseptic conditions with complex agar media by medical personnel. Therefore, none of these devices provide an immediate method for diagnosis of the presence of the high number of yeast associated with a vaginal yeast infection, and none of them are applicable to a test which may be used at home by persons who are not medically trained.

SUMMARY OF THE INVENTION

It is a primary object of the present invention to provide a method and an apparatus for immediate and inexpensive determination of whether the large numbers of yeast associated with vaginal yeast infections are present.

It is a further object of the present invention to provide a method and an apparatus which are easy to use so that a woman may immediately determine whether or not a high number of vaginal yeast are present, indicating a possible yeast infection, or alternatively whether symptoms associated with a yeast infection may be due to some other more serious problem with similar symptoms.

Another object of the present invention is to provide a simple, self-administered, inexpensive, accurate and reliable test system that allows a woman to immediately determine if she has an overgrowth of vaginal yeast to insure that diagnostic data is available before treatment is begun.

A further object of the present invention is to provide a test that indicates whether treatment for yeast infection is inappropriate, thereby saving critical time and indicating that a medical visit is necessary instead.

Briefly, the preferred embodiment of the present invention is a method and apparatus for immediately detecting the presence of high numbers of vaginal yeast which are associated with yeast infections through a method and apparatus which use a sample of vaginal discharge, dyes the yeast present in the discharge with a fluorescent dye specifically sensitive to yeast, and subjects the dye to ultraviolet radiation to determine the level of visible fluorescence. The level of fluorescence indicates the presence or absence of the high number of yeast associated with a vaginal infection.

The attainment of the foregoing and related objects, advantages and features of the invention should be more readily apparent to those skilled in the art after review of the following more detailed description of the invention.

IN THE DRAWING

FIG. 1 is a plan view of the preferred embodiment of a kit for immediate diagnosis of vaginal yeast infections in accordance with this invention; and FIG. 2 is a perspective view of a specimen slide designed for use with this invention.

DETAILED DESCRIPTION OF THE PREFERRED EMBODIMENT

This invention constitutes a method and an apparatus for immediate diagnosis of vaginal yeast infections. With reference to FIG. 1, a yeast detection test kit 10 is shown. Kit 10 includes a kit body with lower test kit body 12 and upper test kit body 14. The test kit body is preferably formed of an inexpensive but durable material, such as plastic. For reasons discussed below concerning the fluorescence method of detection used, the test kit body is preferably black to absorb any stray light and to make the detection method more sensitive by making fluorescence easier to perceive. The test kit body includes a closing tab 16 which attaches a locking piece (not shown) on lower test kit body 12.

Lower test kit body 12 contains the elements of the test kit used in conducting the yeast infection test. These include a fluorescence light housing 18 which includes a fluorescence light bulb 20, on/off switches 22, and a battery (not shown) to supply power to the fluorescence light bulb 20. The preferred embodiment uses near-ultraviolet light to diagnose yeast infections through visible fluorescence of a dyed yeast sample. Therefore, a battery-powered near-UV ultraviolet light is used. An example of a suitable battery-powered fluorescent lamp which has proved suitable is Radio Shack Catalog No. 61-2734, using a black light UV bulb No. F4T5BLB made by WKO, in Japan.

Lower test body 12 also includes a snap-in holder 38 which is used for accurately positioning a specimen slide 40 relative to fluorescence light bulb 20.

Upper test kit body 14 includes the materials necessary for obtaining and preparing a vaginal exudate specimen for testing. Test equipment compartment 28 holds specimen slides 26, cover slips 25, and swabs 24. Cover slips 25 are preferably glass, and swabs 24 are preferably composed of cotton or some other absorbent material. A more detailed view of slides 26 is shown in lower test kit body 12 as slide 40 and in FIG. 2. Specimen slide 40 has an area for a control portion 42 and an area for an exudate portion 44. Preparation of the specimen slide 40 is described in further detail below.

With reference to FIG. 2, an embodiment of a specimen slide 40 is shown in perspective view. A glass or black plastic slide is the present preferred embodiment, but an absorptive slide as shown in FIG. 2 may be used. The absorptive slide includes a top layer 52 which is comprised of a 1 micrometer milipore non-cellulose filter paper, which is dyed black so that fluorescence from the slide is easier to detect. The middle layer 54 is comprised of absorptive filter paper, and the bottom layer 56 is comprised of a rigid fiberboard support.

Referring again to FIG. 1, upper test kit body 14 also includes a solution compartment 30 which holds three bottles of test solution: an alkaline treatment solution 32, a dye solution 34, and a rinse solution 36.

Yeast infection test kit 10 is designed to facilitate simple and immediate diagnosis of yeast infections. The kit allows a woman to perform a test in a quick, simple and private manner.

The following criteria have been established for vaginal yeast infections. Vaginal yeast at levels of less than $10^3$ colony-forming units/milliliter of secretion are normal vaginal flora, not representing yeast infection and are present in up to 50% of the female post-puberty population. Only levels of yeast of $10^4$ colony-forming units/milliliter of secretion or higher constitute the overgrowth of yeast diagnosed as a yeast infection. Therefore, vaginal yeast infection is a relative concentration diagnosis. It takes approximately $10^3$ total yeast/milliliter as determined by direct microscopic hemocytometer count to give one colony-forming unit on a culture plate. Therefore, yeast infection is only present when the total concentration of all yeast cells exceeds approximately $10^7$ yeast/milliliter. Recent studies have measured infection concentrations exceeding $10^9$ colony-forming units/millimeter of exudate.

Specimen slides 26 are packaged in a protective packet, such as plastic or foil, which is preferably airtight and purged with nitrogen to insure a non-contaminated and non-oxidizing environment for the specimen slide 26. The presence of a non-contaminated, non-oxidizing environment is important because specimen slide 26 contains a control portion, as shown in the detail of specimen slide 40 in FIGS. 1 and 2. Control portion 42 of specimen slide 40 contains a concentration of yeast which correlates with the minimum concentration found in vaginal yeast infections. As noted above, a yeast infection is only present when the total concentration of yeast cells exceeds approximately $10^7$ yeast/milliliter. In general, higher numbers of yeast correlate with more severe clinical symptoms, i.e. higher levels of yeast cause a more severe infection. Therefore, control portion 42 holds a standardized yeast sample of approximately $10^7$ yeast/milliliter. The yeast need not be alive. We have found that a control specimen has sufficient lifetime to permit use of a pre-packaged control over an extended time period (exceeding several months), which may be lengthened by use of packaging to retard contamination and aging of the control specimen. Slide 40 preferably includes a notation (on the slide itself or on its packaging) of the expiration date for the control portion 42 of the slide.

This test method measures total yeast concentration by staining the yeast with a dye, calcofluor white, which forms a specific chemical bond to cellulose and chitin in the yeast cell wall. Other biological agents present in vaginal discharges are dissolved in the preparation of the specimen slide. When yeast stained with calcofluor white are exposed to ultraviolet light, a green fluorescence is emitted. At the level of $10^7$ total yeast/millimeter (the concentration of the preferred standardized sample), the fluorescence of the stained sample is easily visible to the naked eye. Higher concentrations, as would occur in more severe yeast infections, are brighter.

The test for yeast infection is conducted as follows. First, a slide 26 is removed from its package and placed on paper towels. A sample of vaginal discharge is obtained with a swab 24, and then the swab is dabbed or rolled over the exudate sample portion 44 of slide 40. This is preferably done 1 or 2 times with the slide, at two-minute intervals. Exudate portion 44 is allowed to dry for approximately four or five minutes.

The exudate portion 44 and control portion 42 of specimen slide 40 are prepared by first applying several drops of an alkaline treatment and wash solution 32 to exudate portion 44 and control portion 42. The alkaline treatment solution preferably consists of approximately 10% by weight potassium hydroxide in water, or a similar alkaline solution such as 10% sodium hydroxide in water. The potassium hydroxide solution dissolves only non-yeast structures. The potassium hydroxide solution is allowed to sit on the sample areas for about thirty seconds. The slide is then tipped on its side to allow any excess solution to run off onto the paper towel.

Next, several drops of dye solution 34, preferably calcofluor white, is added to exudate portion 44 and control portion 42 of specimen slide 40 and allowed to sit for about 30 seconds. Calcofluor white, an optical brightener, is a colorless dye used as a whitening agent in the textile and paper industry. Because it binds to cellulose, chitin, and fungal elements, and fluoresces when exposed to long wavelength UV and short wavelength visible light, it has been used to demonstrate cellulose in microorganisms, stain the cell walls of plants, and to screen specimens for fungal elements. The preferred dye solution utilizes 0.1 gram calcofluor white M2R (Poly-sciences, Inc., Warrington, Pa., or Sigma Chemical Co., St. Louis, Mo.) and 0.05 gram Evans Blue (Sigma Chemical) dissolved in 100 ml distilled water.

After the dye solution has been applied, the slide is again tipped to allow excess solution to run off onto the paper towel. Now, several drops of rinse solution 36, preferably approximately 10% KOH in water (which does not affect calcofluor's binding to yeast), are gently placed on the slide sample areas and allowed to stand flat and still for about thirty seconds. The slide is then tipped on its side again to allow any excess solution to run off onto the paper towel. This further removes any dye not bound to yeast. A cover slip 25 is placed directly on top of the sample portions of specimen slide 40 and allowed to sit for about 5 seconds. The specimen slide 40 is then turned over and gently pressed down on the paper towel to express any excess solution.

Slide 40 is turned right side up and placed into snap-in holder 38, which positions the slide exactly with respect to fluorescence light bulb 20.

Once specimen slide 40 has been prepared, the kit is taken into a darkened room, and the fluorescence light bulb 20 is turned on. The room is preferably as dark as possible so that the eye-sensitivity in viewing the fluorescence of the specimen slide 40 will be as sensitive as possible. Any bluish-green glow coming from the exudate portion 44 of specimen slide 40 is compared visually to the glow coming from the control portion 42 of the specimen slide 40. When the exudate portion 44 and control portion 42 of specimen slide 40 are compared for relative fluorescence, a fluorescence in the exudate portion 44 greater than or equal to the fluorescence of the control portion 42 of the specimen slide indicates the presence of a concentration of yeast which indicates a yeast infection. If the exudate glow is less bright than the glow from the standard sample area, then a diagnosis of vaginal yeast cannot be made with certainty, and the woman should consult a doctor as soon as possible to determine whether or not a more serious infection is present.

The present invention uses both positive and negative results to obtain useful information concerning the possible causes of the vaginal discharge or discomfort. In particular, if a yeast infection is diagnosed, over-the-counter anti-yeast medication can be used. If the test is negative, the woman has been able to eliminate a yeast infection as the cause for a problem and will not be tempted to self-treat for a yeast infection inappropriately, and will be on notice that a more thorough medical test is required.

The test kit 10 of this invention may be used for multiple diagnosis provided that additional specimen treatment solutions 32, 34 and 36, specimen slides 26, swabs 24, and cover slips 25 are provided as required.

We have compared the results obtained with the method and kit of this invention with the results obtained in a medical clinic, which utilize microscopic evaluation of slides to determine the presence of yeast or other agents. In approximately 98% of the cases, we find agreement between our results in diagnosing yeast infection and the clinical microscopic test results.

This invention has been described in terms of a specific dye, calcofluor white, which stains yeast to fluoresce blue-green under ultraviolet light. This system is particularly useful because the excitation light (near UV and short wavelength visible (purple)) is easily distinguished from the fluorescence (blue-green) with the naked eye. However, any dye fluorescence test which correlates specifically with yeast concentration will work suitably well in this method. For example, yeast concentration could be correlated with fluorescence from fluorescein-labeled anti-yeast antibodies in an immuno-fluorescence microscopic technique.

Although the present invention has been described in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A test kit for detecting the presence or absence of levels of yeast associated with vaginal yeast infections comprising:
   (a) a test kit body;
   (b) a specimen slide to which a sample of vaginal exudate may be applied;
   (c) a dye for staining yeast in said sample of vaginal exudate, said dye capable of fluorescing in the presence of a light source;
   (d) a light source mounted within said test kit body for exciting fluorescence in said dye;
   (e) a control specimen which when exposed to said light source has a level of fluorescence corresponding to the fluorescence from a known concentration of yeast; and
   (f) means for positioning said specimen slide and said control specimen with respect to said light source, whereby fluorescence may be detected from a dye-stained sample of vaginal exudate and compared with fluorescence from said control specimen, to determine whether said sample of vaginal exudate contains levels of yeast associated with vaginal yeast infections.

2. The test kit of claim 1, wherein the dye is calcofluor white.

3. The test kit of claim 1, further comprising an alkaline solution for treating the sample of vaginal exudate prior to staining the sample with said dye.

4. The test kit of claim 3, wherein the dye is calcofluor white.

5. The test kit of claim 1, wherein the control specimen holds a standardized yeast sample for comparison with said sample of vaginal exudate.

6. The test kit of claim 5, further comprising an alkaline solution for treating the sample of vaginal exudate prior to staining the sample with said dye.

7. The test kit of claim 5, wherein the dye is calcofluor white.

8. The test kit of claim 7, further comprising an alkaline solution for treating the sample of vaginal exudate prior to staining the sample with said dye.

9. The test kit of claim 8, further comprising a swab for obtaining said sample of vaginal exudate and applying said sample to said specimen slide.

10. The test kit of claim 9, wherein the test kit body is black.

11. A method for immediate detection of the presence or absence of levels of yeast associated with vaginal yeast infections comprising:
    (a) obtaining a sample of vaginal exudate;
    (b) staining yeast in said sample with a fluorescent dye;
    (c) exposing said stained sample to a light source capable of exciting fluorescence in said dye; and
    (d) comparing fluorescence of said stained sample with the level of fluorescence from a control specimen having a level of fluorescence corresponding to the fluorescence from a known concentration of yeast.

12. The method of claim 11, wherein the fluorescence is visible light of sufficient intensity for detection with the naked eye.

13. The method of claim 11, wherein said dye is calcofluor white.

14. The method of claim 11, further comprising the step of treating the sample with an alkaline solution prior to staining the sample with said dye.

15. The method of claim 11, wherein the control specimen contains a known concentration of yeast, and the yeast in said control specimen are stained with said dye at approximately the sample time as yeast in said sample are stained.

16. The method of claim 15, wherein said dye is calcofluor white.

17. The method of claim 15, wherein the fluorescence is visible light of sufficient intensity for detection with the naked eye.

18. The method of claim 15, further comprising the step of treating the sample and control specimen with an alkaline solution prior to staining the sample and control specimen with said dye.

19. The method of claim 18, wherein said dye is calcofluor white.

20. The method of claim 18, wherein the fluorescence is visible light of sufficient intensity for detection with the naked eye.

* * * * *